United States Patent [19]

Mochida et al.

[11] Patent Number: 4,850,710

[45] Date of Patent: Jul. 25, 1989

[54] METHOD OF MEASURING AND DISPLAYING DOUBLE REFRACTION OCCURRING IN A MATERIAL TO BE MEASURED

[75] Inventors: Yoshihiro Mochida; Takeyuki Sugimoto; Ichiro Shirahama; Naoshi Kiyomoto, all of Tokyo, Japan

[73] Assignee: ORC Manufacturing Co., Ltd., Tokyo, Japan

[21] Appl. No.: 101,242

[22] Filed: Sep. 25, 1987

[30] Foreign Application Priority Data

Sep. 26, 1986 [JP] Japan .................................. 228814/61

[51] Int. Cl.$^4$ ............................................. G01N 21/23
[52] U.S. Cl. ..................................... 356/367; 356/426
[58] Field of Search ............... 356/364, 365, 366, 367, 356/368, 369, 426

[56] References Cited

U.S. PATENT DOCUMENTS 4,309,110 1/1982 Tumerman ........................ 356/366

Primary Examiner—F. L. Evans
Attorney, Agent, or Firm—Cushman, Darby and Cushman

[57] ABSTRACT

Disclosed is a method of measuring and displaying double refraction. In this method measuring light which has been subjected to double refraction passes through the material to be measured at a point of measurement thereof. A surface of the material to be measured is disposed in a manner that the same is located at right angles, or is inclined with respect to an optical axis of the measuring light. The material is rotated about the point of measurement thereof on a plane which is perpendicular to the optical axis of the measuring light. The data on the double refraction is displayed together with a plus or minus sign thereof as a function of the angle of rotation, in the form of polar coordinates corresponding to the angle of rotation.

3 Claims, 6 Drawing Sheets

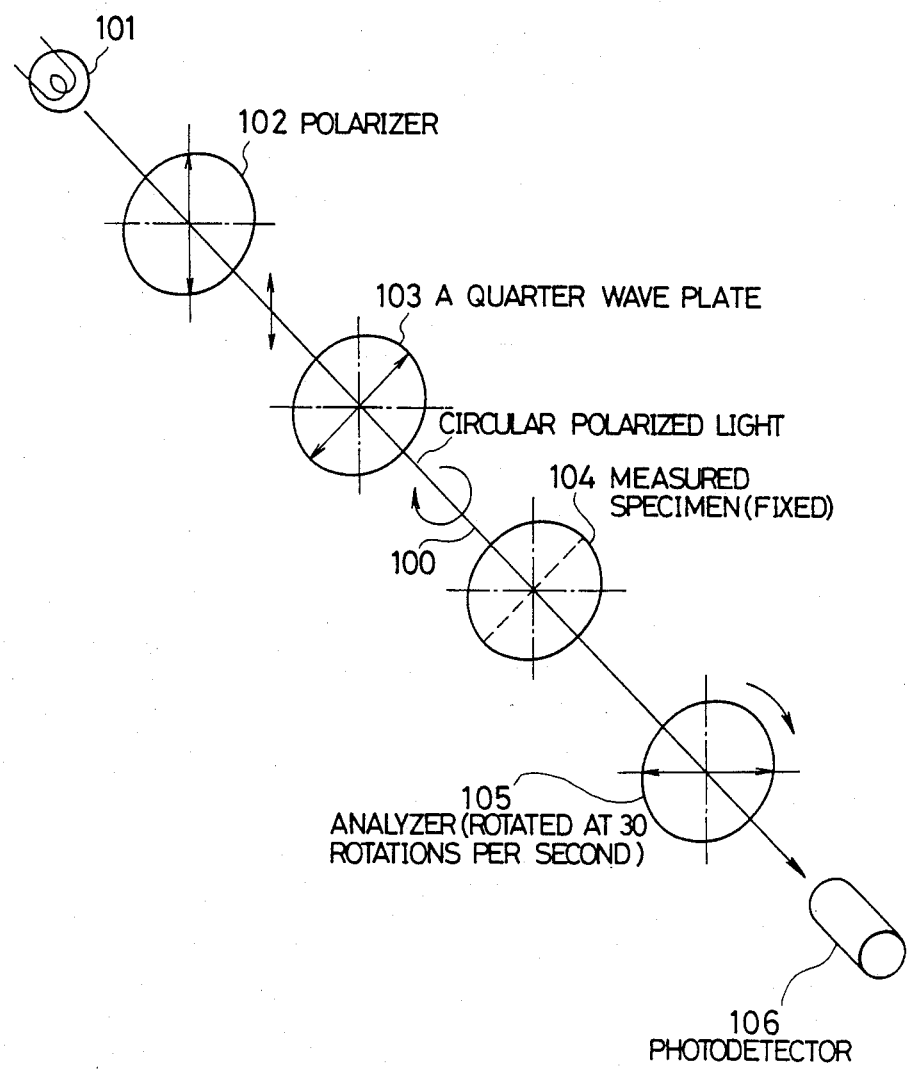

METHOD OF MEASURING AND DISPLAYING DOUBLE REFRACTION OCCURRING IN A MATERIAL TO BE MEASURED

BACKGROUND OF THE INVENTION

1. FIELD OF THE INVENTION

The present invention relates to a method of measuring and displaying double refraction occurring in a material to be measured, which makes it possible to obtain the data on molecular orientation of the molecular chain in the material by determining the double refraction and the double refraction fast axis in the same.

2. DESCRIPTION OF THE PRIOR ART

In almost all of the materials such as calcite capable of transmitting light in which crystals or molecular chains are arranged, light which has entered the material becomes two refracted light rays, i.e., is subjected to double refraction. There has in recent years been a demand for a double refraction measuring technique which is intended to measure, by utilizing such double refraction, the fast axis, i.e., molecular chain axis deviation having occurred, in a high polymeric material.

A conventional apparatus for measuring double refraction occurring in a material to be measured is constructed as shown in FIG. 7. Measuring light 100 is prepared by causing light emitted from a light source 101 to be circularly polarized by passing it through a polarizer 102 and a quarter wave plate 103. A conventional method of measuring double refraction occurring in the material consisted in causing the measuring light 100 to be passed through a fixed material specimen 104, detecting the resulting measuring light 100 by means of a photodetector 106 such as a photomultiplier after passing it through an analyzer 105 arranged to rotate at approximately 30 rotations per second, and performing a Fourier analysis or the detected signal to determine the ellipticity of the measuring light, thus to determine the maximal value and its plus or minus sign of the double refraction.

With the above-mentioned conventional double-refraction measuring method, however, it was entirely impossible to obtain, from such a maximum value or a sign of double refraction, information on molecular orientation, i.e., information concerning in what direction an orientation angle of the main axis of a molecular chain or a plus or minus sign corresponds on a measured specimen. When a discussion is made on the molecular chain axis deviations involved in a high-polymeric substrate material such as an optical memory storage disk, it has recently been inevitably necessary to obtain such data on molecular orientation. Thus, the absence of any prior art technique serving such purpose has become a great problem.

SUMMARY OF THE INVENTION

The present invention has been made in view of the above-mentioned problems and the object thereof is to provide a method of measuring and displaying double refraction occurring in a material to be measured, which makes it possible to obtain the data on molecular chain axis orientation in the material.

To attain the above object, according to the present invention, there is provided a method of measuring and displaying double refraction occurring in a material to be measured, by causing measuring light to pass through the material to be measured at a point of measurement thereof, which comprises the step of disposing a surface of the material to be measured in a manner that the same is located at right angles, or is inclined, with respect to an optical axis of the measuring light, the step of causing the material to rotate about the point of measurement thereof on a plane which is perpendicular to the optical axis of the measuring light, and the step of displaying the data on the double refraction together with a plus or minus sign thereof as a function of the angle of rotation, in the form of polar co-ordinates corresponding to the angle of rotation.

In the present invention, the material to be measured is caused to rotate, whereby the magnitude, including its plus or minus sign, of the double refraction occurring therein are determined as a function of the angle of rotation, both the magnitude and its plus or minus sign thus being displayed in the form of polar co-ordinates corresponding to the angle of rotation. The magnitude of the double refraction displayed in the form of polar co-ordinates is expressed in the form of a curve shown in FIG. 5 which has four maximal and minimal values in corresponding relationship to the angle of rotation. Therefore, a line which connects together two opposite maximal values each bearing a plus sign is referred to as "fast axis". Generally, in a high polymeric substance, this "fast axis" corresponds to the direction indicated by the principal axis of the molecular chain. For this reason, determining the direction of such a fast axis makes it possible to immediately determine the data on molecular orientation such, as those indicating in what direction on the material to be measured the principal axis of the molecular chain is directed.

BRIEF DESCRIPTION OF THE DRAWINGS

FIG. 7 is an illustration for explaining a conventional double-refraction measuring apparatus.

DESCRIPTION OF THE PREFERRED EMBODIMENTS

An embodiment of the present invention will now be described in detail with reference to the drawings.

Figure 1:
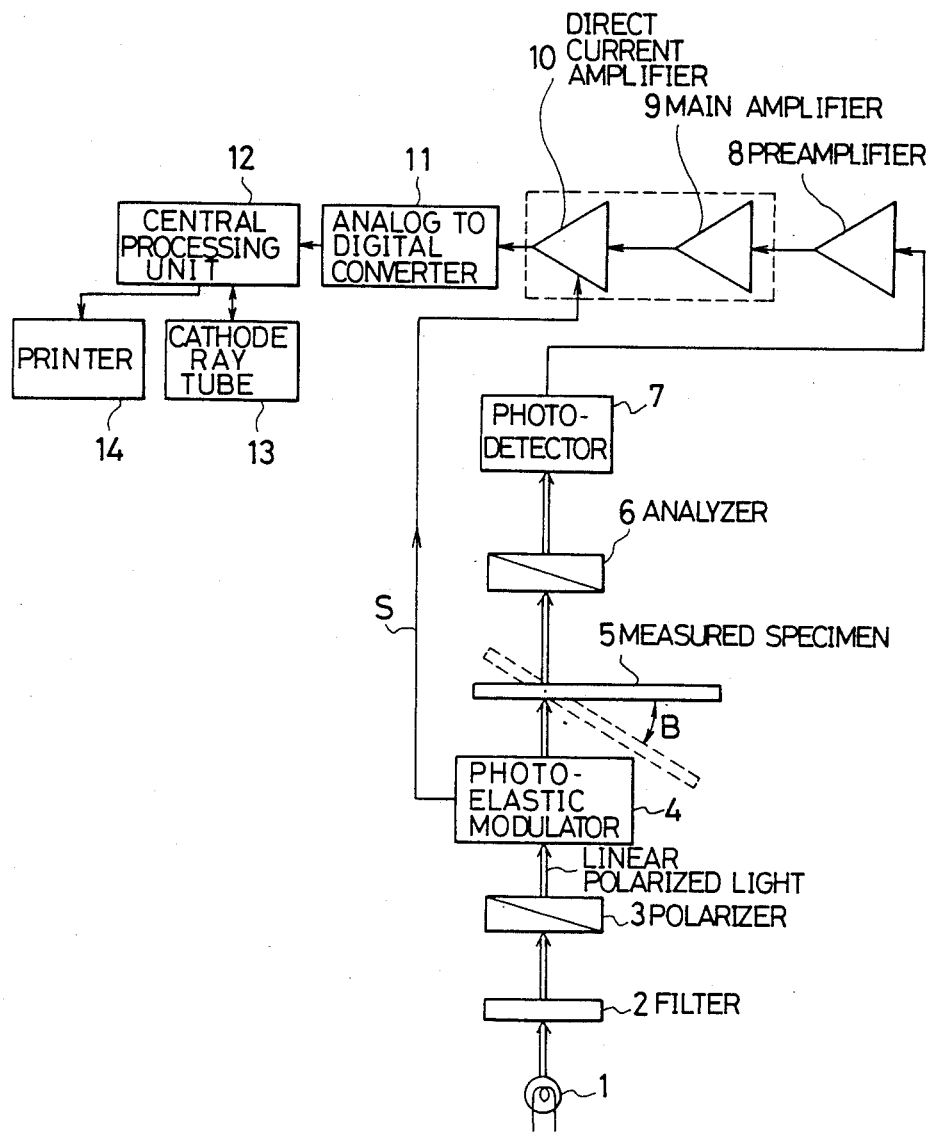
FIG. 1 is a block diagram of an apparatus for measuring and displaying the double refraction occurring in a material to be measured, embodying the present invention.

Referring to FIG. 1, which is a block diagram of an apparatus for measuring and displaying the double refraction occurring in a material to be measured, embodying the present invention, light which has been emitted from a light source 1 such as a He-Ne laser (having a wavelength of 633 nm), a semiconductor laser (having a wavelength of 780 nm or 830 nm), or a Xenon lamp is allowed to pass through a filter 2. The light ray then becomes linear polarized light by passing through a polarizer 3 such as a Glan-Thompson prism to enter a photoelastic modulator (P.E.M.) 4. This photoelastic modulator 4 is so arranged as to apply as a modulation signal to the medium an alternating current electric field which has a frequency of, for example, 50 KHz to cause the phase difference in the light to vary within the range of from 0 to ¼ wavelength. The light which has entered the photoelastic modulator 4 is modulated thereby into measuring light which continuously changes with time from linear polarized light into circular polarized light, and again from circular polarized light to linear polarized light. When this measuring light has been incident upon a material specimen 5 to be measured and passed through the same, its ellipticity is varied on a delicate basis due to double refraction. The light, the ellipticity of which exhibits such a delicate variation, is converted into an electric photocurrent signal in the form of alternating current by being passed to a photodetector 7 such as a photomultiplier by way of a fixed analyzer 6. It is to be noted that the specimen 5 is caused to rotate about its measuring point on a plane which is perpendicular to the optical axis of the measuring light.

The above-mentioned photocurrent signal is amplified by a preamplifier 8 and also by a main amplifier 9 of lock-in amplification system into an alternating current and then is further amplified in the form of direct current by a direct current amplifier. In the lock-in amplification system, the phase sensitive detection is performed using the modulation signal from the photoelastic modulator 4 as a reference signal S. More specifically, of the detected photocurrent signals, only the modulated signal components are selectively amplified while non-modulated components including the photocurrent produced by light other than those in the form of signals, dark current, etc. do not become a measuring output signal. As a result, the measuring output signal thus amplified has a great value of S/N, providing highly precise measured results. Since, in this embodiment, the photoelastic modulator is employed as a light modulator, the photocurrent signal from the photodetector 7 such as a photomultiplier contains the variations in ellipticity, as they stand, which have occurred due to double refraction in the interior of the specimen 5. For this reason, while the conventional double-refraction measuring method provided a measuring precision of ±1 nm at best, this embodiment can be expected to provide a measuring precision of ±0.01 nm. Therefore, the invention can cope with a required measuring precision of ±0.1 nm which is necessary for measurement of double refraction in, for example, an optical memory storage disk.

Figure 5:
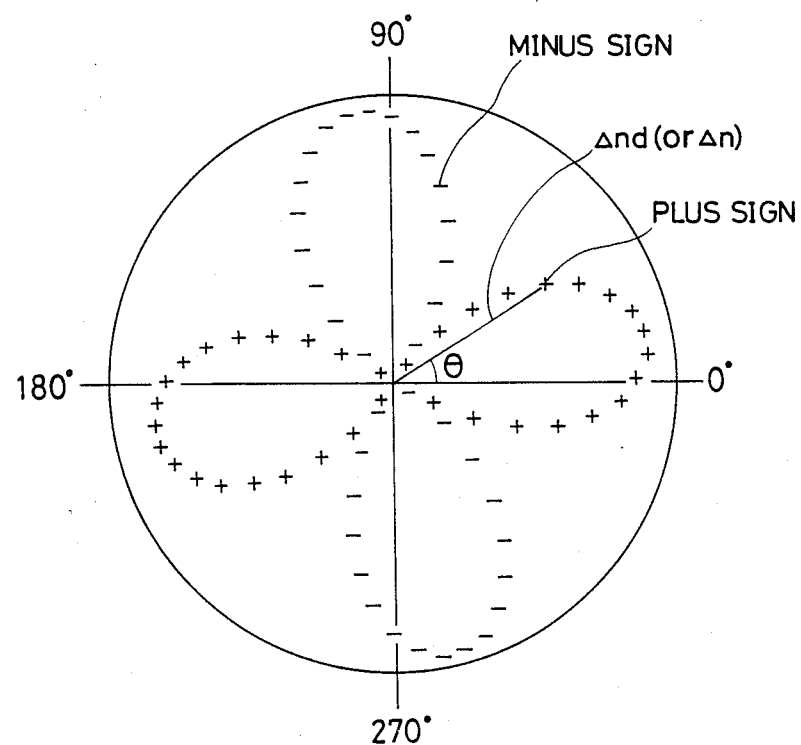
FIG. 5 shows, by way of example, double refraction as displayed in the form of polar co-ordinates.

The photocurrent signal which has been amplified as above in the form of direct current is converted into a digital signal by an analog to digital converter 11, and then is inputted into a computer 12, The computer 12 can immediately determine the ellipticity from the direct current components, fundamental component (50 KHz), first harmonic component (100 KHz) of such digital signal, to thereby determine the double-refraction and its plus or minus sign in the form of a function of the angle of rotation $\theta$ of the specimen 5. Then, the angle of rotation $\theta$, the magnitude of the corresponding double refraction and its plus or minus sign are displayed on a display 13 or printer 14 such as CRT, in the form of polar co-ordinates, as shown in FIG. 5. The printer 14 may be other printing means such as, for example, an XY plotter.

Figure 2:
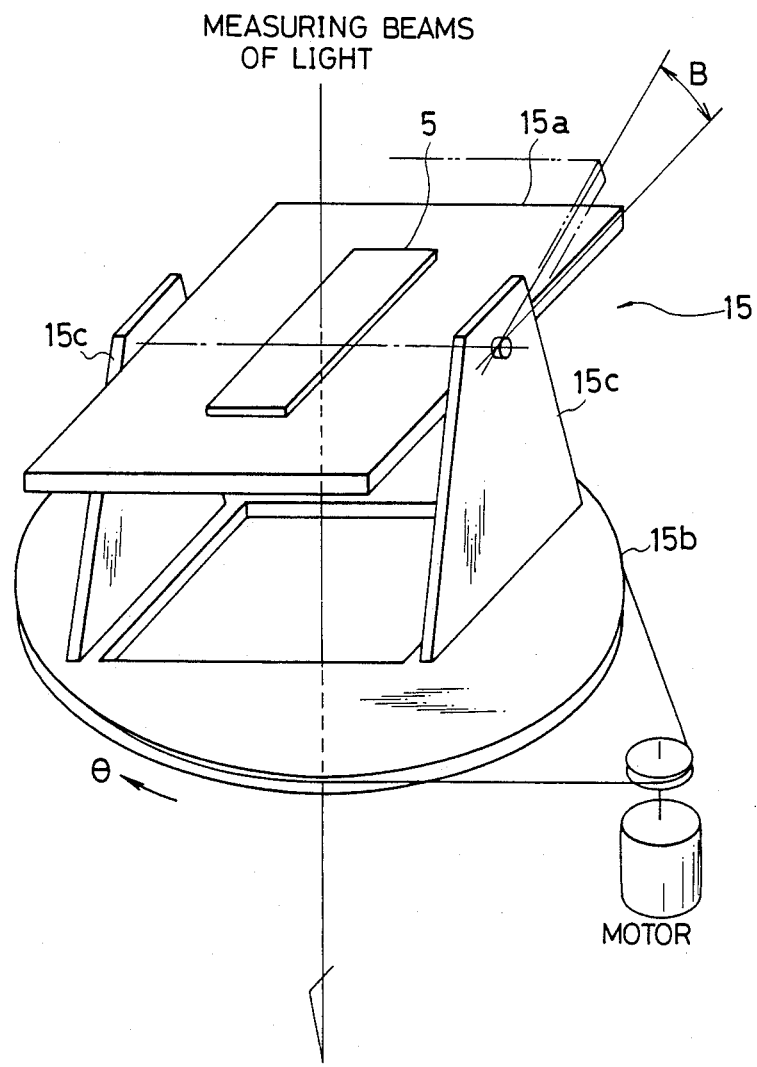
FIG. 2 is a perspective view of a specimen mounting means embodying the present invention.

FIG. 2 is a perspective view of a specimen mounting means embodying the present invention. The specimen mounting means 15 has a measuring stage 15a which is arranged to hold the specimen 5 in place by using a suitable holding structure, the measuring stage 15a being tiltably supported by stage supporting members 15c, 15c fixed onto a rotary table 15b, via shafts. By use of this measuring stage 15a, the specimen 5 can be measured in a state wherein its surface for measurement is made perpendicular, or is inclined, with respect to the axis of the measuring light. The specimen 5 is inclined at an angle with respect to the optical axis and is subjected to measurement of the double refraction. The measured results are compared with those which have been obtained through the measurements made at right angles or other angles, to thereby obtain data on the molecular orientation in the specimen 5 as taken in the thicknesswise direction thereof.

Figure 3:
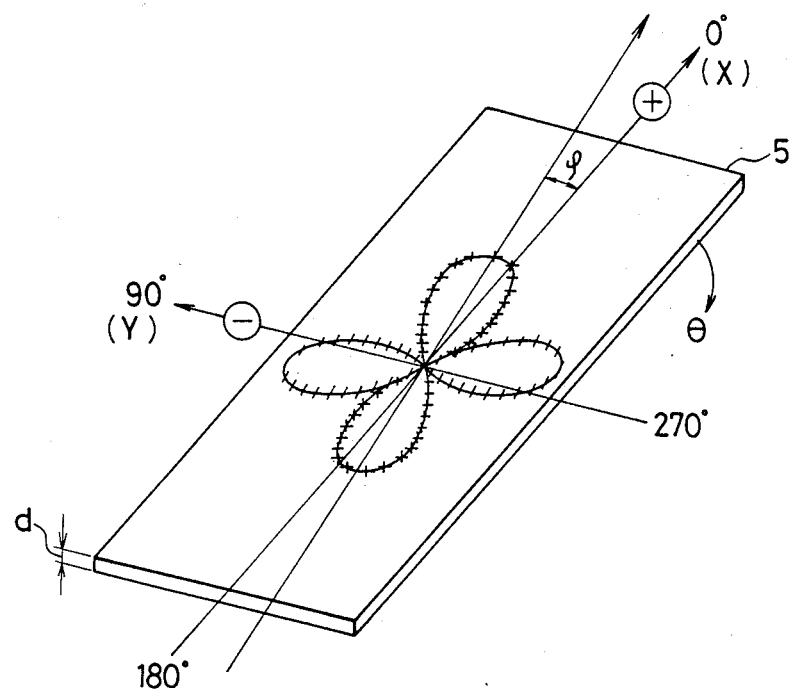
FIG. 3 is an illustration for explaining measured results of the double refraction having occurred in a material to be measured.

The operation of this embodiment having the described construction will now be described. FIG. 3 is an illustration for explaining measured results of the double refraction having occurred in a specimen to be measured. As stated before, the measured results are displayed on, for example, the printer 13 in the form of polar co-ordinates as shown in FIG. 5. In FIG. 3, however, the measured results are shown, for brevity, on an imaginary basis in a manner that they are drawn directly on the upper surface of the specimen 5 in corresponding relationship to the same. X and Y represent reference co-ordinates axes for the measuring light. At the time when measurement is started, such reference co-ordinates axes are made to go along with the reference directions for manufacturing the specimen 5, respectively. It would be convenient to cause the specimen 5 to be rotated with such reference direction being made 0°. The magnitude of the double refraction is expressed in terms of double refraction index $\Delta n$ or phase difference in double refraction $\Delta nd$ (where d represents the thickness of the specimen). When the refraction index in the X direction is represented by $n_x$ and that in the Y direction by $n_y$, the double refraction index $\Delta n$ can be expressed, by the formula $\Delta n = n_x - n_y$. A plus or minus sign may be applied to the value of $\Delta n$ and $\Delta nd$ in accordance with the value of $n_y$ relative to $n_x$. Even when the data on the double refraction is displayed in the form of polar co-ordinates by using any one of $\pm \Delta n$ and $\pm \Delta nd$, it may be so done as shown in FIG. 5. When this is viewed in FIG. 3, the direction (fast axis) indicated by a straight line, which connects a center of the four-leaved clover like configuration and a positive or negative maximal value on the curvilinear line describing the clover, indicates the direction of the principal axis of the molecular chain in the specimen. Thus, the data on molecular orientation are immediately seen at one view in FIG. 5. The plus or minus sign suitably is set, in advance of measurement, using a phase plate or the like, such that the fast axis, i.e., the direction of the principal axis of the molecular chain in the specimen is a positive direction.

Figure 4:
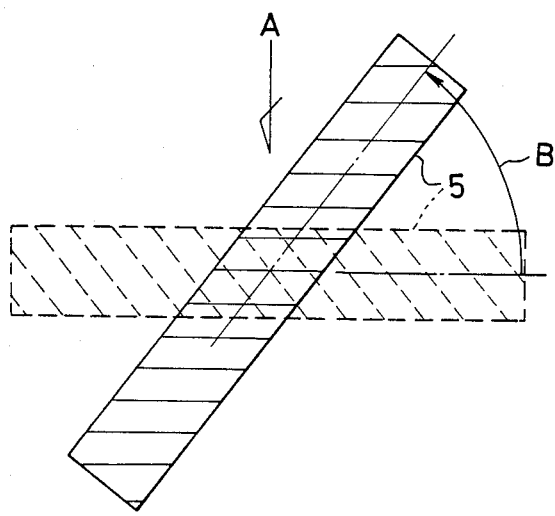
FIG. 4 is an illustration for explaining a material to be measured.

According to the specimen, the direction of the principal axis of the molecular chain is in some cases inclined in the thicknesswise direction as indicated in FIG. 4 by oblique lines, which shows a section of the specimen. In such cases, the specimen 5 is inclined at an angle B toward the optical axis A from the direction which intersects the optical axis A at right angles thereto. Thereafter, as stated before, the specimen is rotated under such condition on a plane which is perpendicular to the optical axis of the measuring light, thereby measuring and displaying the double refraction. The angle of inclination B would sufficiently serve the purpose if it can be set at ±30°. The difference in the measurement results obtained with an inclination angle of B from those obtained with an inclination angle of 90° or other is shown, although the difference is dependent upon the specimen. A comparison between the results allows the information on the molecular orientation concerning the direction towards the thickness of the specimen to be obtained.

Figure 6:
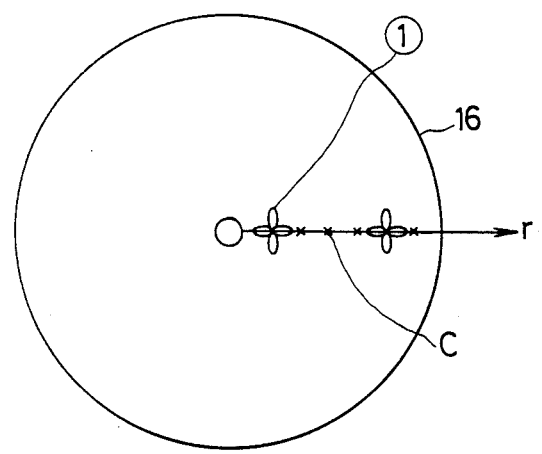
FIGS. 6A and 6B shows views of explaining one example of measurements in which the invention has been applied to measurement of the molecular chain axis deviation made in an optical memory storage disk.
Figure 6:
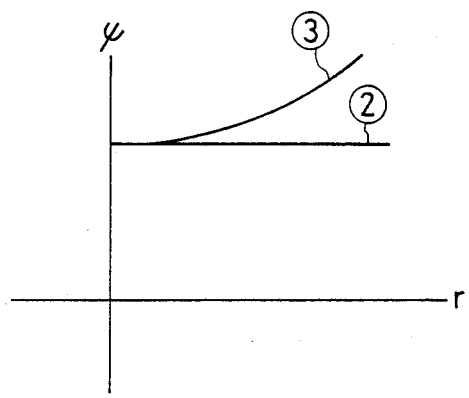

FIG. 6 shows views for explaining one example of measurement in which the invention has been applied to the measurement of the molecular chain axis deviation made in a substrate of an optical memory storage disk. the mark x which has been indicated in FIG. 6(a) by a symbol c shows a point of measurement located on an optical memory storage disk 16. The points of measurement each of which is marked x are suitably set in a radial direction r. At each point of measurement c, as shown, the measured result (1) of the above-mentioned four-leaved clover like configuration is obtained. The use of these measured results (1) makes it possible to determine, by way of computer, a graph or the like which shows that the angle of orientation $\psi$ of the principal axis of the molecular chain as taken with respect to the radial direction r is uniform as at (2), or is curved as at (3). The use of these results makes it possible, when the optical memory storage disk is manufactured by pressing, to optimumly adjust the parameters such as the ratio of blending materials involved, the speed at which the materials are poured or charged into a mold involved, etc. while the measured results are being taken into consideration. This makes it possible not only to enhance the quality of the resulting products but also to cause an increase in the manufacturing yield.

The present invention is not limited to the above-mentioned embodiment but permits various applications and modifications to be made without departing from the spirit and scope of the invention. That is, measurement per se of the double refraction may be made by and other method if it is made by rotating the specimen to measure the double refraction as a function of this angle of rotation.

As has been described above, according to the present invention, when measuring the double refraction, the specimen to be measured is rotated, whereby the double refraction is displayed as a function of the angle of rotation in the form of polar co-ordinates. Therefore, not only the absolute value of the magnitude of the double refraction, but also the direction and the angle of orientation of the principal axis of the molecular chain, in the specimen to be measured can be appreciated at one view.

What is claimed is:

1. A method of measuring and displaying double refraction occurring in a material to be measured comprising the following steps:

passing measuring light through a photoelastic modulator resulting in measuring modulated light;

passing said modulated light through said material to be measured at a point of measurement thereof;

disposing a surface of said material to be measured in a manner that the same is located at right angles, or is inclined, with respect to an optical axis of said measuring light;

rotating said material about said point of measurement thereof on a plane which is perpendicular to the optical axis of the measuring light producing double refraction;

passing said measuring light to a photodetector, measuring variations in ellipticity resulting in a measurement of double refraction; and displaying said double refraction together with a plus or minus sign thereof as a function of the angle of rotation, in the form of polar coordinates corresponding to the angle of rotation.

2. The method of claim 1 wherein said step of passing measuring light through a photoelastic modulator further includes modulating the light continuously, changing the light with time from linear polarized light into circular polarized light, and again from circular polarized light to linear polarized light at high speed.

3. The method of claim 1 wherein said material to be measured is physically oriented and multiple measurements taken, to obtain the molecular orientation of the material in the direction perpendicular to the material.

* * * * *